United States Patent [19]
Choi

[11] Patent Number: 5,758,642
[45] Date of Patent: Jun. 2, 1998

[54] IMPROVED GAS DELIVERY MASK

[76] Inventor: Myung Ja Choi, 4332 Ivy La., Glenview, Ill. 60025

[21] Appl. No.: 724,923

[22] Filed: Oct. 2, 1996

[51] Int. Cl.⁶ .................................................. A62B 7/00
[52] U.S. Cl. ...................... 128/206.21; 128/206.24; 128/206.27; 128/206.28; 128/207.11; 128/205.25
[58] Field of Search ............... 128/206.21, 206.23, 128/206.24, 206.27, 206.28, 207.11, 207.18, 203.22, 203.29, 205.25, 206.11, 911, 912, DIG. 26

[56] References Cited

U.S. PATENT DOCUMENTS

| | | | |
|---|---|---|---|
| D. 250,047 | 10/1978 | Lewis et al. | 128/205.25 |
| 2,260,701 | 10/1941 | Boothby et al. | |
| 2,323,199 | 1/1943 | Bulbulian | 128/206.24 |
| 2,625,155 | 1/1953 | Engelder | 128/207.11 |
| 2,675,803 | 4/1954 | Kaslow | |
| 2,928,387 | 3/1960 | Layne | |
| 4,201,205 | 5/1980 | Bartholomew | |
| 4,231,363 | 11/1980 | Grimes | |
| 4,328,797 | 5/1982 | Rollins, III et al. | |
| 4,458,679 | 7/1984 | Ward | 128/205.25 |
| 4,573,463 | 3/1986 | Hall | 128/207.11 |
| 4,580,556 | 4/1986 | Kondur | 128/912 |
| 4,848,334 | 7/1989 | Bellam | 128/207.11 |
| 4,938,209 | 7/1990 | Fry | 128/200.21 |
| 5,233,978 | 8/1993 | Callaway | |
| 5,357,945 | 10/1994 | Messina | 128/911 |
| 5,400,781 | 3/1995 | Davenport | 128/205.25 |
| 5,429,683 | 7/1995 | Le Mitouard | |
| 5,474,060 | 12/1995 | Evans | 128/205.25 |
| 5,586,551 | 12/1996 | Hilliard | 128/203.22 |
| 5,649,533 | 7/1997 | Oren | 128/206.21 |
| 5,657,752 | 8/1997 | Landis et al. | 128/207.12 |

*Primary Examiner*—Vincent Millin
*Assistant Examiner*—William J. Deane, Jr.
*Attorney, Agent, or Firm*—Welsh & Katz, Ltd.

[57] ABSTRACT

A face mask for the delivery of a gas to a patient includes a body portion forming an open sided chamber having a peripheral edge for contacting the face of the patient. The body portion has an integrally formed nose portion and chin portion and increases in width from the nose portion toward the chin portion giving the body portion generally triangular shape. A nose portion has a reduced dimension such that a contour of the nose portion conforms to the contour of the nose of the patient forming a sealing fit therebetween. The nose portion has an upper end terminating in all apex extending toward the bridge of the nose and is configured to contact the nose at a point substantially below the bridge of the nose so as to eliminate interference between the nose portion and the eyes of the patient. An elastic strap is secured proximal the peripheral edge of body portion to retain the face mask against the face of the patient. The elastic strap is affixed along the upper end of the nose portion proximal the apex and meets the face mask at an angle such that the upward urging of the face mask is substantially eliminated. A chin portion is formed proximal the lower end of the nose portion and includes a forward peripheral wall depending from a horizontal shelf of the nose portion. The peripheral wall is configured to contact a forward portion of the chin of the patient. The chin portion also includes a skirt formed about the forward peripheral wall that depends inwardly toward the patient and is configured to receive the chin of the patient.

9 Claims, 3 Drawing Sheets

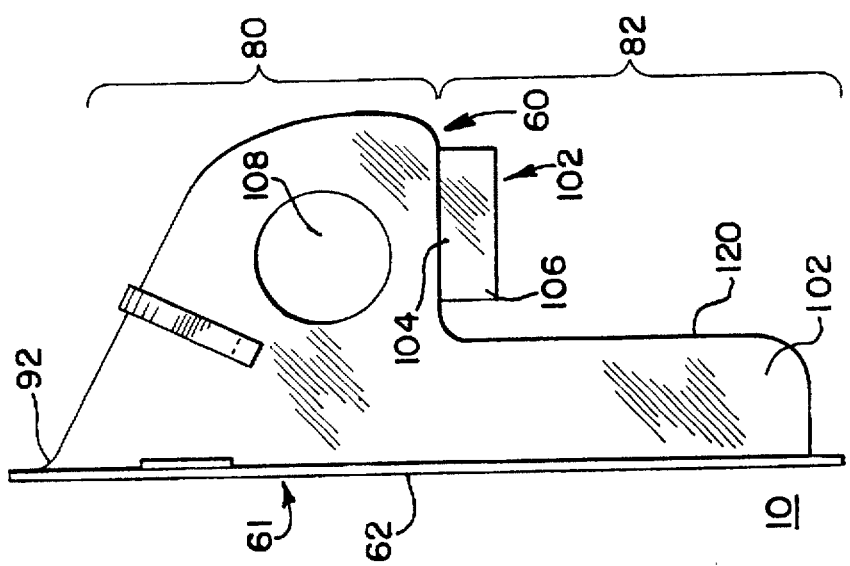
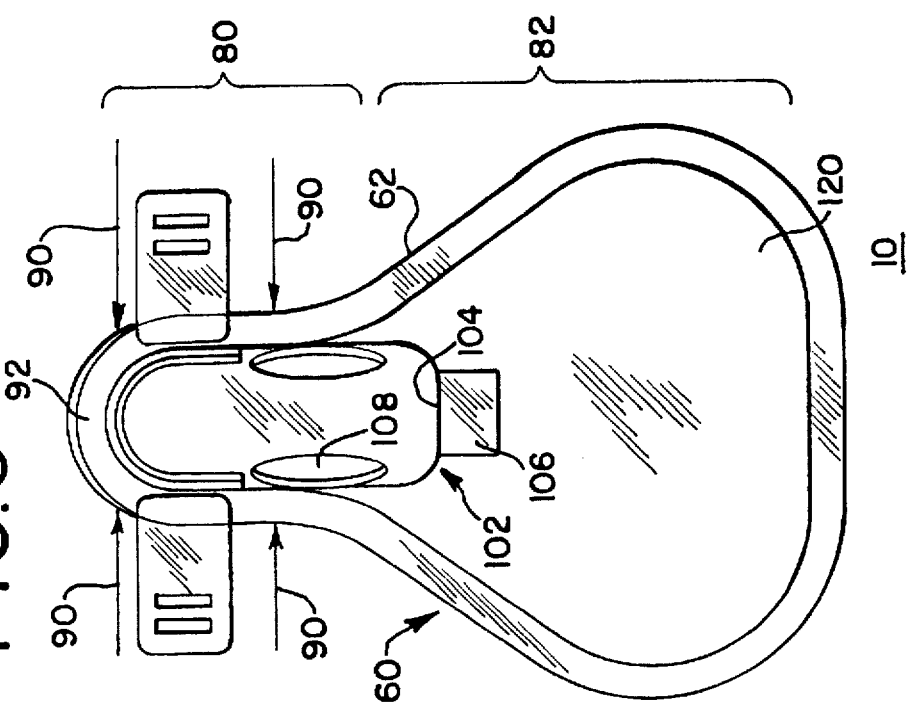

IMPROVED GAS DELIVERY MASK

BACKGROUND OF THE INVENTION

The present invention relates generally to the field of masks, and more specifically to masks which are used to administer a gas, such as oxygen, to a patient.

The administration of gas, and particularly oxygen, to a patient is often unsatisfactory. The administration, regulation, and efficiency are very poor since a relatively unknown volume of oxygen is often delivered. One reason is that many masks do not form an adequate seal with the patient's face. This may either be due to the general shape of the mask or the positioning of the mask on the patient's face. Additionally, typical masks are uncomfortable to wear and often interfere with the patient's field of view. As a result, most masks are improperly repositioned by the patient in an attempt of increase user comfort.

Typical face masks are particularly problematic for patients who wear eyeglasses or spectacles. Not only does the mask block the patient's field of view, but the upper portion of the mask that contacts the nose displaces the eyeglass frame rendering use of the eyeglasses difficult or impossible. The patient is forced to either readjust the spectacle frame to a non-ideal position, or to readjust the face mask to permit proper positioning of the eyeglasses. Readjustment of the face mask may place the mask in an awkward or uncomfortable position, and may interfere with the proper delivery of oxygen or other gas. Improper delivery of oxygen can be extremely serious and if prolonged, may result in hypoxia. This may result in medial complications and increased medical costs.

Most gas delivery masks are secured to the face with an elastic band or strap. Typically, the strap is secured around the patient's neck or head and attaches to the face mask along an outside edge. Generally, the straps attach to the face mask at about the midpoint of the mask. This has significant drawbacks. When the strap is secured around the patient's head, the strap is typically placed just over the ears. The strap forms a downward angle from the ears to the attachment point on the mask. Since the strap is disposed at an angle, the elastic or spring action of the strap tends to cause the mask to "ride up" or "creep" along the face until it interferes with the patient's vision. This is uncomfortable and represents a potential health risk, as it may cause tissue damage or irritation to the eye area.

Gas delivery masks are also used to deliver humidified gas or air to the patient. The humidified gas or air appears as a thick fog or mist. It has been found that when the mask is positioned in an improper position, such as when the mask has "crept" upward on the patient's face, many patients, particularly elderly patients, experience fear and anxiety when the fog or mist escapes from the mask and approaches the eyes. Such patients may refuse to wear the mask under these conditions.

Examples of known masks are disclosed in U.S. Pat. Nos. 4,201,205 (Bartholomew), 4,231,363 (Grimes), 4,32 8,797 (Rollins III), and 5,400,781 (Davenport). However, these previously known masks do not include the overall combination of structural and operational features of the instant invention which together provide a mask which can be comfortably used by patients and which does not interfere with the eyes or eyeglasses of the user.

Accordingly, it is an object of the present invention to substantially overcome the above described problems.

It is another object of the present invention to provide a novel face mask that does not interfere with the eyes or eyeglasses of the patient such that the mask can be used in combination with eyeglasses.

It is a further object of the present invention to provide a novel face mask that is secured to the patient's face by a strap disposed in a position so that the mask does not tend to shift position on the patient's face.

It is also an object of the present invention to provide a novel face mask having a nose portion that contacts the patient's nose substantially below the bridge of the nose.

It is still an object of the present invention to provide a novel face mask having an enlarged chin portion to facilitate proper seating against the chin of the patient.

SUMMARY OF THE INVENTION

The disadvantages of present face masks are substantially overcome with the present invention by providing a novel improved gas delivery mask. The face mask includes a nose portion that only extends partially along a portion of the nose of the patient. The nose portion terminates in an apex which contacts the nose approximately halfway between the bridge of the nose and the tip of the nose. Additionally, the nose portion "hugs" the contour of the nose and does not laterally extend toward the eyes of the patient. This permits the patient to wear eyeglasses or spectacles since the spectacles may be positioned in the usual way without interference from the nose portion of the face mask. This significantly improves user comfort and provides less incentive for the patient to remove or adjust the face mask.

The elastic strap which secures the face mask to the patient's face attaches to the upper portion of the nose portion and permits the strap to be disposed in a flat or horizontal angle relative to the patient's head. This eliminates the tendency for the face mask to "creep" upward under elastic tension of the strap. Known face masks are attached to the strap at about the midpoint of the mask causing the strap to be disposed at an upward angle. This tends to pull the mask upward and eventually causes interference with the patient's vision. The present invention eliminates this problem. The present improved gas delivery mask is configured to remain attached to the patient's face and facilitate the proper delivery of gas, such as oxygen. Since proper delivery of gas is maintained, medical complications resulting from the improper delivery of gas are eliminated. This may reduce overall medical costs and improve patient comfort and satisfaction.

More specifically, the face mask of the present invention includes a body portion forming an open sided chamber having a peripheral edge for contacting the face of the patient. The body portion is configured to overlie the face of the patient, including overlying a portion of the patient's nose, mouth, and chin. The body portion has an integrally formed nose portion and chin portion where the body portion increases in width from the nose portion toward the chin portion. Accordingly, the body portion has a generally triangular shape.

The nose portion has a reduced dimension such that a contour of the nose portion conforms to the contour of the nose of the patient forming a sealing fit therebetween. The nose portion has an upper end terminating in an apex extending toward the bridge of the nose and is configured to contact the nose at a point substantially below the bridge of the nose so as to eliminate interference between the nose portion and the eyes of the patient. The nose portion has a lower end terminating in a substantially horizontal shelf which includes a coupling downwardly depending from the shelf. The coupling is configured to be releasably coupled to a gas supply tube for supplying the gas to the patient. The nose portion includes a pair of apertures arranged to admit a naso-gastiric tube or a nasal suction tube into an interior portion of the nose portion for insertion into the nostril of the patient. Also included is an elastic strap secured proximal the peripheral edge of the body portion to retain the face mask against the face of the patient. The elastic strap is affixed along the upper end of the nose portion proximal the apex and meets the face mask at an angle such that the upward urging of the face mask is substantially eliminated.

The chin portion is formed proximal the lower end of the nose portion and includes a forward peripheral wall depending from the horizontal shelf of the nose portion where the peripheral wall is configured to contact a forward portion of the chin of the patient. The chin portion has a skirt formed about the forward peripheral wall where the skirt depends inwardly toward the patient. The chin portion is configured to receive the chin of the patient.

BRIEF DESCRIPTION OF THE DRAWINGS

The features of the present invention which are believed to be novel are set forth with particularity in the appended claims. The invention, together with further objects and advantages thereof, may best be understood by reference to the following description in conjunction with the accompanying drawings.

FIG. 5 is a side elevational view of a specific embodiment of the face mask shown in FIG. 1; and FIG. 6 is a front elevational view of a specific embodiment of the face mask shown in FIG. 1.

DETAILED DESCRIPTION OF THE INVENTION

Figure 1:
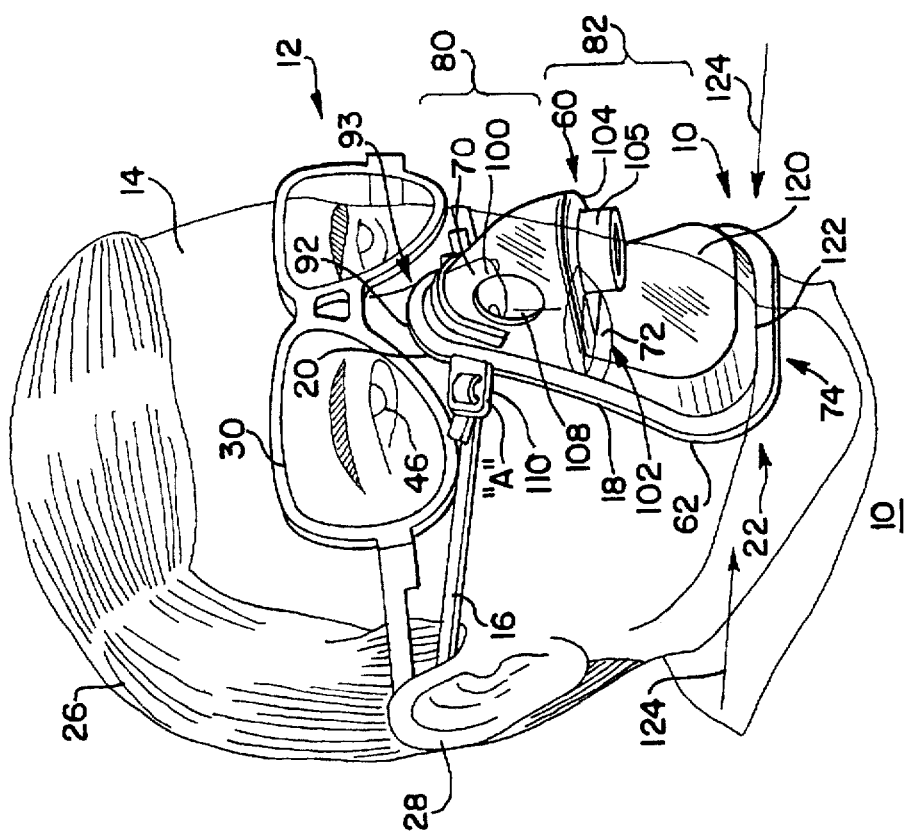
FIG. 1 is a perspective view of a specific embodiment of a face mask shown in an operative position.
Figure 2:
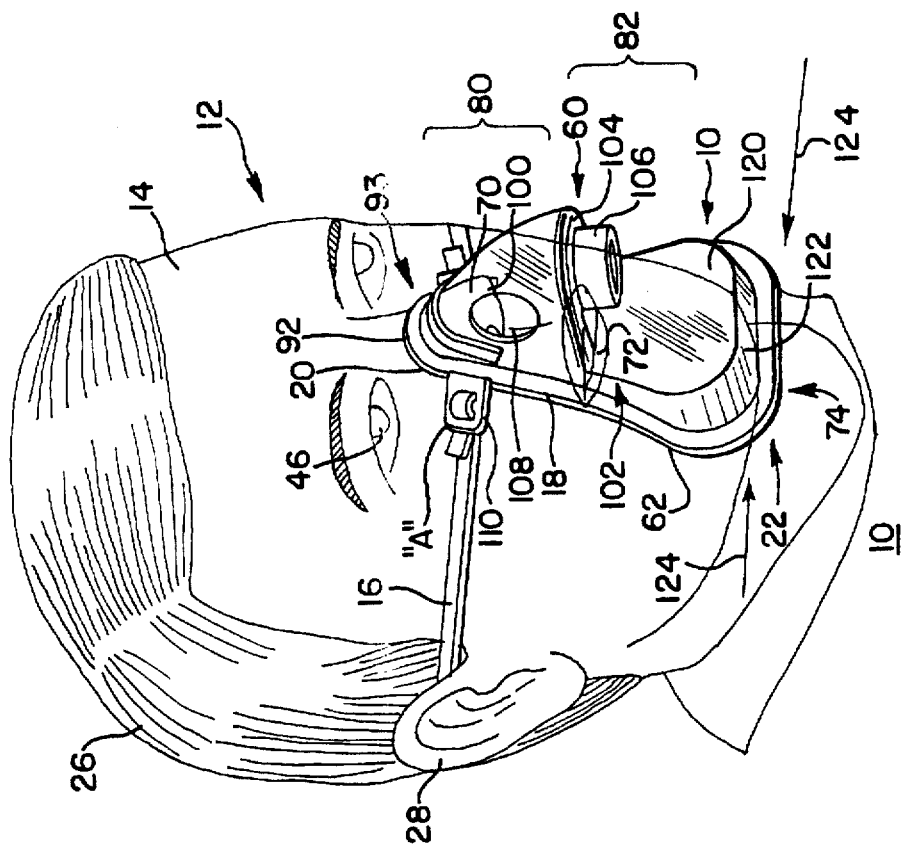
FIG. 2 is a perspective view of a specific embodiment of the face mask shown in FIG. 1, particularly illustrating simultaneous use of the face mask and eyeglasses by the patient.

Referring now to FIGS. 1 and 2, a face mask 10 is shown general placed about a face 12 of a user or patient 14. An elastic strap or band 16 is shown fastened to a peripheral edge 18 of the face mask 10 at a point near the top edge 20 of the face mask. The attachment point is labeled as reference letter "A." The elastic strap 16 is arranged to encircle the back of the patient's head 26 and may, for example, pass just above the patient's ears 28. Note that in FIG. 2, the patient 14 is shown wearing eyeglasses or spectacles 30.

Figure 3:
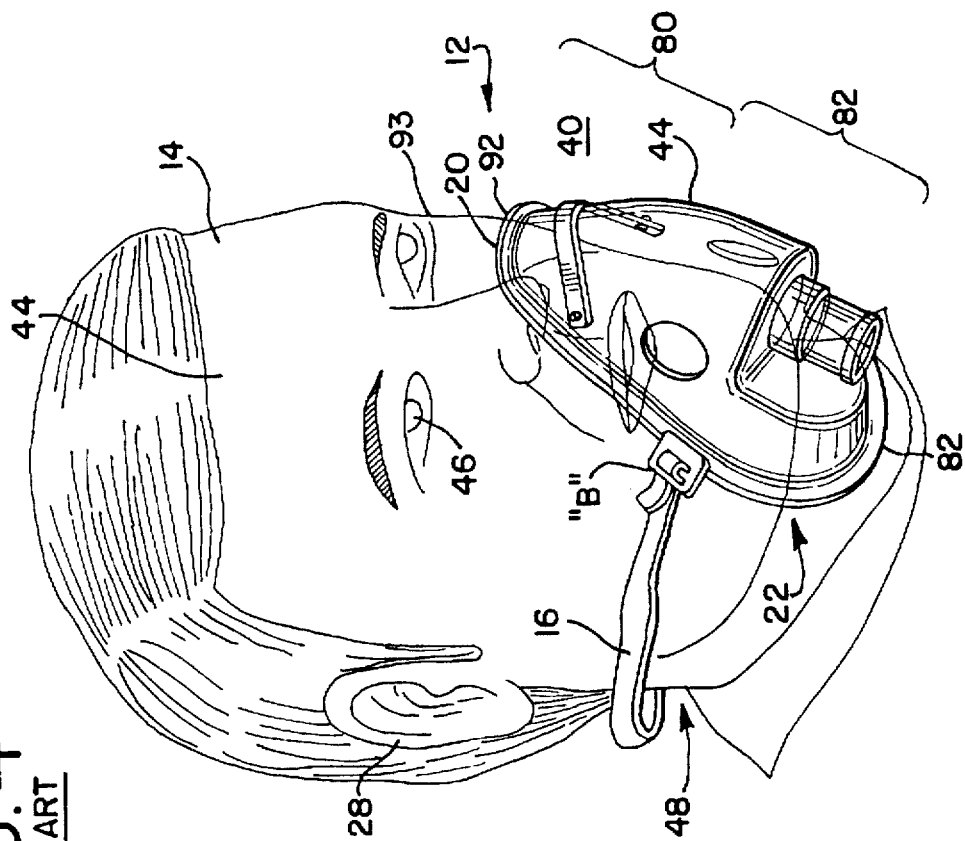
FIGS. 3 and 4 are perspective views of a prior art face mask.
Figure 4:
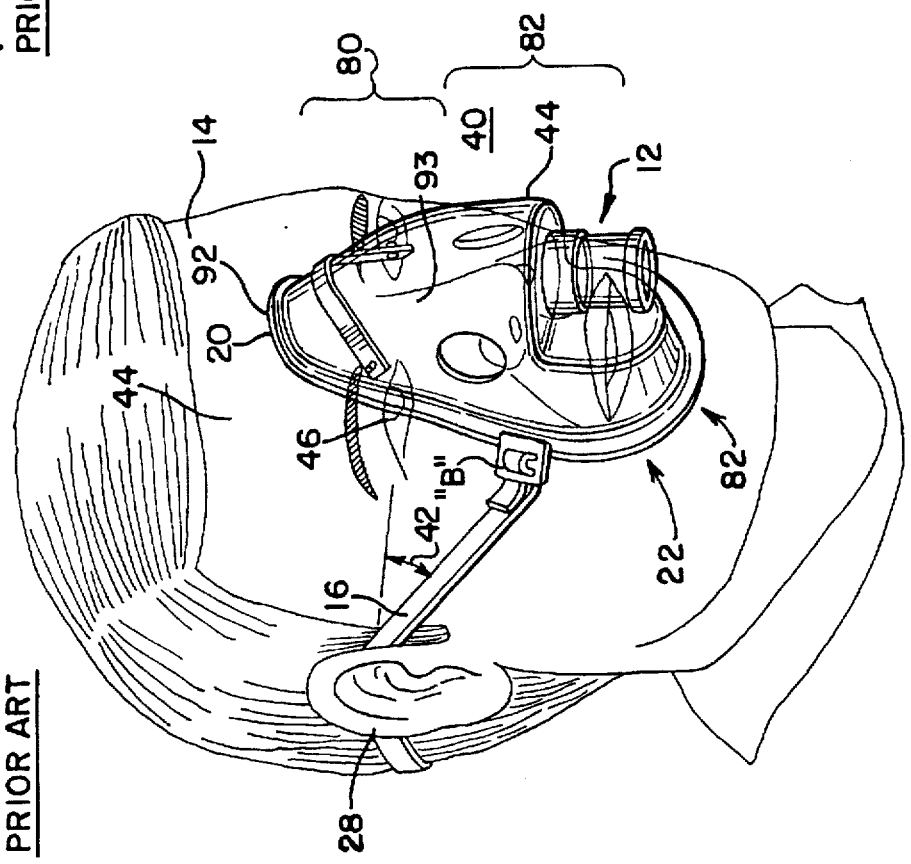

Referring now to FIGS. 3 and 4, like reference numerals are used to denote like structures. In FIGS. 3 and 4, a known mask 40 is shown held in place on the patent's face 12 with the elastic strap 16. The strap 16 is shown fastened to the mask 40 at a point about half way between the top edge 20 and the bottom edge 22 of the face mask 40. The attachment point is labeled with reference letter "B." Because the attachment point "B" is generally in the middle of the face mask 40 relative to its length, and because the elastic band 16 generally meets the ears 28 of the patient 14, the elastic band is disposed at a downward angle 42 relative to the face 12 of the patient 14, as shown in FIG. 3. This downward angle 42 causes the face mask 40 to be pulled or urged upward toward the forehead 44 of the patient 14. This is uncomfortable for the patient 14 and may even pose a health risk. When the face mask 40 is pulled upward or "creeps" upward under the elastic force of the strap 16, the patient's vision becomes blocked as the face mask covers a portion of the eyes 46. At best, this is inconvenient and uncomfortable requiring the patient 14 to readjust the face mask 40. At worst, if the patient 14 is unable to adjust the face mask 40, the eyes 46, the lower eyelids, or the facial area may become damaged or irritated.

As shown in FIG. 4, the prior art face mask 40 may also be worn in an alternate arrangement where the elastic strap 16 is secured around the back of the patient's neck 48. However, this arrangement is also unsatisfactory since head movement tends to cause the elastic strap 16 to slide into a position where slack develops, causing the face mask 40 to come loose from the patient's face 12. In this situation, the patient 14 may fail to receive proper gas delivery. This may result in adverse health consequences and costly medical complications.

Referring now to FIGS. 1-2 and 5-6, the face mask 10 according to the present invention facilitates the delivery of a gas to the patient 14 and maintains proper orientation on the patient's face 12. The face mask 10 includes a body portion 60 forming an open sided chamber 61 (FIG. 5) that permits the face mask to be placed over face 12 of the patient 14. The face mask 10 is formed from a unitary section of plastic or other elastic material, preferably from a single plastic sheet. As shown in the figures, the face mask 10 terminates in a peripheral edge 62 which circumscribes the entire perimeter of the face mask. The peripheral edge 62, like the material from which the entire face mask 10 is formed, is soft and pliable so as to conform to the contour of the patient's face 12. It is also sufficiently strong and stiff so as to retain its shape so that it forms a seal where it contacts the patient's face 12 (FIGS. 1-2). The body portion is configured to overlie the patient's face 12 and overlies a portion of the patient's nose 70, mouth 72, and chin 74 (FIGS. 1-2). The body portion 60 forms a seal with the face 12 of the patient to facilitate the delivery of gas to the patient with minimal loss, as will be described hereinafter.

The body portion 60 has an integrally formed nose portion 80 and a chin portion 82. The body portion 60 generally increases in width from the nose portion 80 toward the chin portion 82 providing a generally triangular shape. This "triangular" shape provides significant advantages relative to the generally oblong prior art masks, such as those shown in FIGS. 3-4. The nose portion 80 has a generally reduced dimension or width such that the contour of the nose portion conforms generally to the contour of the nose 70 of the patient 14. The reduced dimension or width of the nose portion 80 is clearly shown in FIG. 6 and is labeled as arrow 90. This is significantly different from known masks which simply provide a bulbous enclosure large enough to accommodate a typically sized nose, as will be described in greater detail hereinafter. Although not drawn to scale in FIGS. 1,2 and 6, the nose portion is of a reduced width to essentially "hug" the contour of the nose.

The nose portion 80 has an upper end terminating in an apex 92 extending toward a bridge 93 of the nose 70. The apex 92 is configured to contact the nose 70 at a point substantially below the bridge 93 of the nose so as to eliminate interference between the nose portion 80 and the eyes 46 of the patient 14. Prior art face masks 40, such as the face masks shown in FIGS. 3-4, are formed such that the apex 92 extends upward and contacts the bridge 93 of the nose. Also, in known configurations, the nose portion 80 diverges or spreads out or widens along the nose. As shown in the prior art face masks of FIGS. 3-4, it is clear that the nose portion 80 extends upward and contacts the bridge 93 of the nose while at the same time, diverges or spreads laterally to contact the face or cheeks. Such a configuration renders wearing eyeglasses or spectacles 30 (see FIGS. 1–2) difficult or impossible. Eyeglasses 30 typically rest either directly on the nose or have nose pads which extend from the bridge of the frame to rest on the nose. The nose portion 80 of known face masks 40 (FIGS. 3–4) precludes use of the eyeglasses 30 since the eyeglasses cannot properly rest on top of the nose portion 80 material which extends toward the eyes 46. For proper orientation of the eyeglasses 30, the material forming the face mask 10 must not extend toward the areas upon which the eyeglasses are seated.

Referring to FIGS. 1–2 and 5–6, because the apex 92 of the nose portion 80 contacts the nose 70 of the patient 14 at a point about half way between the bridge 93 of the nose and a tip 100 of the nose, and because the nose portion has a reduced width 90 (FIG. 6) along the nose 70, the patient 14 may easily wear eyeglasses 30 without interference from the nose portion 80. As clearly shown in FIG. 2, the material forming the face mask 10, and in particular, the nose portion 80, is disposed away from the eyes 46 of the patient 14 permitting the spectacle frames 30 to be worn by the patient without contacting the nose portion.

The nose portion 80 has a lower end 102 terminating in a substantially flat horizontal shelf 104. The horizontal shelf 104 is disposed directly under the nostrils of the patient to permit the delivery of the gas, as will be described in greater detail hereinafter. The shelf 104 is integrally formed with the nose portion 80 and is inwardly directed toward the neck of the patient. The shelf 104 substantially parallel to a plane defined to pass through the eyes 46 of the patient 14 and the upper portion of the ears 28 of the patent. The shelf 104 includes a coupling 106 downwardly depending from the shelf which permits access to the interior portion of the nose portion 80. T he coupling 106 is configured to be releasably coupled to a gas supply tube (not shown) for supplying the gas to the patient 14.

The nose portion 80 also includes pair of apertures 108 formed through the material of the nose portion. The apertures 108 are positioned just under the nostrils of the nose and are arranged to admit a naso-gastiric tube or a nasal suction tube (not shown) into the interior portion of the nose portion for insertion into the nostril of the patient.

As described above, the elastic strap 16 is secured to the peripheral edge 18 of the body portion 60 and more particularly, to the peripheral edge associated with the nose portion 80. The strap 16 may be fastened to tabs 110 which are, in turn, attached to the peripheral edge 18 by means known in the art. The strap 16 is affixed along the upper end of the nose portion 80 proximal the apex 92. This is a significant feature since attachment to the nose portion toward the apex 92 causes the strap to assume an essentially "flat" or horizontal angle relative to the face. As shown in FIGS. 1–2, the strap 16 is positioned behind the ears 28 and extends forwardly along the face 12 of the patient 14 until it attaches to the face mask proximal the apex 92. Since the strap 16 is not disposed at an angle, there is no upward urging of the face mask 10. Accordingly, once the face mask 10 is positioned on the patient 14 and the strap 16 is secured about the patient's head, the face mask will not "creep" upward and will remain in place. In the operative position, the strap 16 is substantially parallel to a plane defined to pass through the eyes 46 of the patient 14 and the upper portion of the ears 28.

The face mask 10 includes the chin portion 82 which is formed proximal the lower end 102 of the nose portion 80.

The chin portion 82 has a forward peripheral wall 120 depending from the horizontal shelf 104 of the nose portion 80 at substantially a right angle. However, the angle may be varied without affecting operation of the face mask 10. The peripheral wall 120 is configured to contact a forward portion or front portion of the chin 74. A skirt 122 is formed about the forward peripheral wall 120 and depends inwardly toward the neck of the patient 14. The chin portion 82 is configured to receive the chin 74 of the patient 14. Since the skirt 122 is inwardly directed relative to the chin 74 of the patient 14, the chin portion 82 sealingly contacts an under portion of the chin. Additionally, the forward peripheral wall 120 of the chin portion 82 has an increased width relative to a width of the nose portion, as shown by reference arrows 124 in FIGS. 1–2. The increased width 124 of the chin portion 82, in part, provides the face mask 10 with the generally triangular shape. Such an increased width 124 provides several advantages. First, patient comfort is increased since the patient may more easily move his or her jaw from side to side without restriction. Second, the skirt 122 is able to contact a larger portion of the patient's chin such that an improved seal is created.

Note that such a seal is not an airtight seal, as such seals would need to follow the contour of the face exactly. The seals described herein permit only a small proportion of the gas delivered to the patient to escape, while the great majority of the gas is delivered to the patient via the gas delivery tube (not shown). The curved shape of the skirt 122 generally follows the curved contour of the chin so that a sealing fit between the chin portion 82 and the chin 74 of the patient is achieved. Since the gas delivery tube is coupled to the horizontal shelf 104 of the nose portion 80, and because the horizontal shelf is proximal the nostrils of the patient 14, an air tight seal around the chin 74 is not required for proper delivery of the gas.

A specific embodiment of an improved gas delivery mask according to the present invention has been described for the purpose of illustrating the manner in which the invention may be made and used. It should be understood that implementation of other variations and modifications of the invention and its various aspects will be apparent to those skilled in the art, and that the invention is not limited by the specific embodiment described. It is therefore contemplated to cover by the present invention any and all modifications, variations, or equivalents that fall within the true spirit and scope of the basic underlying principles disclosed and claimed herein.

What is claimed is:

1. A face mask for the delivery of a gas to a patient, the mask comprising:

a body portion forming an open sided chamber having a peripheral edge configured to contact the patient, the body portion arranged to overlie the face of the patient, including overlying a portion of the patient's nose, mouth, and chin;

the body portion having an integrally formed nose portion and chin portion, said body portion increasing in width from the nose portion toward the chin portion, said body portion having a generally triangular shape;

the nose portion having laterally inward reduction in width at a point below the bridge of the nose such that a contour of the nose portion conforms to the contour of the nose of the patient forming a sealing fit therebetween;

the nose portion having an upper end terminating in an apex extending toward the bridge of the nose and configured to contact the nose at a point substantially below the bridge of the nose so as to eliminate interference between the nose portion and the eyes of the patient;

the nose portion having a lower end terminating in a substantially horizontal shelf, said shelf including a coupling downwardly depending from the shelf, said coupling configured to be releasably coupled to a gas supply tube for supplying the gas to the patient;

the nose portion including a pair of apertures arranged to admit at least one of a naso-gastiric tube and a nasal-suction tube into an interior portion of the nose portion for insertion into the nostril of the patient;

an elastic strap secured proximal the peripheral edge of body portion to retain the face mask against the face of the patient, the elastic strap affixed along the upper end of the nose portion proximal the apex said strap meeting an upper portion of the ears of the patient forming a substantially right angle with a vertical centerline of the body portion, said angle of the strap relative to the body portion configured to substantially eliminate upward urging of the face mask;

the chin portion formed proximal the lower end of the nose portion and having a forward peripheral wall depending from the horizontal shelf of the nose portion, said peripheral wall configured to contact a forward portion of the chin of the patient; and the chin portion having a skirt formed about the forward peripheral wall, said skirt depending inwardly toward the patient, and configured to receive the chin of the patient.

2. The face mask according to claim 1 wherein the apex of the nose portion contacts the nose of the patient at a point substantially below the bridge of the nose such that material forming the face mask is disposed away from the eyes of the patient permitting spectacle frames to be worn by the patient without contacting the nose portion of the face mask.

3. The face mask according to claim 1 wherein the apex of the nose portion contacts the nose of the patient at a point about half way between the bridge of the nose and the tip of the nose.

4. The face mask according to claim 1 wherein a width of the nose portion defined between the apex and the lower end of the nose position has a reduced width corresponding to a width of the nose of the patient such that material forming the nose portion of the face mask is inwardly disposed toward the nose so as not to contact a spectacle frame worn by the patient.

5. The face mask according to claim 1 wherein the elastic strap is configured to extend over and behind both ears of the patient such that the strap is substantially parallel to a plane defined to pass through the eyes of the patient and through an upper portion of the ears of the patent, so that upward urging of the face mask relative to the eyes of the patient is substantially eliminated.

6. The face mask according to claim 1 wherein the skirt of the chin portion is inwardly directed relative to the chin of the patient to sealingly contact an under portion of the chin of the patient.

7. The face mask according to claim 1 wherein the forward peripheral wall of the chin portion has an increased width relative to a width of the nose portion, said increased width providing the face mask with the generally triangular shape, said chin portion configured to receive the chin of the patient.

8. The face mask according to claim 1 wherein the forward peripheral wall of the chin portion has an increased width relative to a width of the nose portion, said increased width providing the face mask with the generally triangular shape, said chin portion providing a seal between the chin portion and the chin of the patient.

9. The face mask according to claim 1 wherein the forward peripheral wall of the chin portion has a curved contour configured to follow a contour of the chin of the patient to facilitate a sealing fit between the chin portion and the chin of the patient.

* * * * *